(12) United States Patent
Ben Mamoun et al.

(10) Patent No.: US 8,128,921 B2
(45) Date of Patent: Mar. 6, 2012

(54) USE OF CONDITIONAL PLASMODIUM STRAINS LACKING NUTRIENT TRANSPORTERS IN MALARIA VACCINATION

(75) Inventors: Choukri Ben Mamoun, Farmington, CT (US); Kamal El Bissati, Chicago, IL (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 11/827,282

(22) Filed: Jul. 11, 2007

(65) Prior Publication Data

US 2008/0026010 A1 Jan. 31, 2008

Related U.S. Application Data

(60) Provisional application No. 60/830,371, filed on Jul. 11, 2006.

(51) Int. Cl.
*A01N 63/00* (2006.01)
*A01N 65/00* (2006.01)
*A61K 48/00* (2006.01)
*A61K 39/38* (2006.01)

(52) U.S. Cl. .................. 424/93.1; 424/93.2; 424/93.21; 424/184.1; 424/265.1; 424/268.1; 424/269.1

(58) Field of Classification Search .................. None
See application file for complete search history.

(56) References Cited

U.S. PATENT DOCUMENTS

| | | | |
|---|---|---|---|
| 4,435,386 A | 3/1984 | Ribi et al. | |
| 4,436,727 A | 3/1984 | Ribi | |
| 4,436,728 A | 3/1984 | Ribi et al. | |
| 4,505,899 A | 3/1985 | Ribi et al. | |
| 4,505,900 A | 3/1985 | Ribi et al. | |
| 4,520,019 A | 5/1985 | Ribi et al. | |
| 4,579,945 A | 4/1986 | Schwartzman et al. | |
| 4,866,034 A | 9/1989 | Ribi | |
| 4,877,611 A | 10/1989 | Cantrell | |
| 5,583,112 A | 12/1996 | Kensil et al. | |
| 5,616,491 A | 4/1997 | Mak et al. | |
| 5,912,000 A | 6/1999 | Podolski et al. | |
| 5,965,144 A | 10/1999 | Podolski et al. | |
| 5,980,912 A | 11/1999 | Podolski et al. | |
| 6,146,632 A | 11/2000 | Momin et al. | |
| 6,194,388 B1 | 2/2001 | Kreig et al. | |
| 6,207,646 B1 | 3/2001 | Kreig et al. | |
| 6,239,116 B1 | 5/2001 | Krieg et al. | |
| 6,339,068 B1 | 1/2002 | Kreig et al. | |
| 7,122,179 B2 * | 10/2006 | Kappe et al. .................. | 424/93.1 |
| 2005/0208078 A1 | 9/2005 | Hoffman et al. | |

FOREIGN PATENT DOCUMENTS

| WO | WO-0387322 A2 | 10/2003 | |
|---|---|---|---|
| WO | 2004/045559 | * | 6/2004 |
| WO | WO 2005/063991 | * | 7/2005 |

OTHER PUBLICATIONS

Ellis, R.W. (Chapter 29 of "VACCINES" [Plotkin, S.A. et al. (eds) published by W. B. Saunders company (Philadelphia) in 1988.*
Oplinger et al NIH record vol. LVII No. 9.*
Matuscheswski et al FEBs Journal 274 :4680-4687, 2007.*
Frevert et al. N. Engl J Med 353: (15) 1600-1602, 2005.*
Clyde et al. Specificity of Protection of Man Immunized against Sporozoite-induced falciparum Malaria. The American Journal of the Medical Sciences vol. 266:398-403, 1973.*
Bissati et al. PNAS Jun. 13, 2006 vol. 103 p. 9286-9291.*
Struik and Riley, Immunological Reviews 2004, vol. 201:268-290.*
Frevert et al. N. Engl J Med, 2005, 353: (15) 1600-1602.*
Sijwali et al. PNAS Mar. 30, 2004 vol. 101, p. 4384-4389.*
Hayward et al (Molecular and Biochemical Parasitology Vo. 107, issue 2, pp. 224-240, Apr. 2000).*
Santiago, Teresa, PhD. vol. 6606B of Dissertations Abstracts International, p. 2912. 173 pages, Dec. 2005.*
Kirk, K. Acta Tropica vol. 89, Issue 3, Feb. 2004, pp. 285-298).*
Fandeur et al. Am. J. Trop. Med. Hyg., 58(2), 1998, p. 225-231.*
"Who Expert Committee on Malaria", *WHO Technical Report Series 892, i-v* 2000 , 1-74.
Boleti, Haralabia et al., "Molecular Identification of the Equilibrative NBMPR-sensitive (es) Nucleoside Transporter and Demonstration of an Equilibrative NBMPR-insensitive (ei) Transport Activity in Human Erythroleukemia (K562) Cells", *Neuropharmacology*, vol. 36, No. 9 1997 , 1167-1179.
Carter, Nicola S. et al., "Isolation and Functional Characterization of the PfNT1 Nucleoside Transporter Gene from *Plasmodium falciparum*", *The Journal of Biological Chemistry*, vol. 275, No. 14, Apr. 7, 2000, 10683-10691.
Carter, Nicola S. et al., "Nucleoside transporters of parasitic protozoa", *Trends in Parasitology*, vol. 17, No. 3 Mar. 2001 , 142-145.
Daddona, Peter E. et al., "Human Adenosine Deaminase", *The Journal of Biological Chemistry*, vol. 22, No. 1 Jan. 10, 1977, 110-115.
Duraisingh, Manoj T. et al., "Negative selection of *Plasmodium falciparum* reveals targeted gene deletion by double crossover recombination", *International Journal for Parasitology*, 32 2002 , 81-89.
El Bissati, K. et al., "The plasma membrane permease PfNT1 is essential for purine salvage in the human malaria parasite *Plasmodium falciparum*", Proceedings of the National Academy of sciences of the United States of America Jun. 13, 2006 , vol. 103(24), 9286-9291.

(Continued)

*Primary Examiner* — Oluwatosin Ogunbiyi
(74) *Attorney, Agent, or Firm* — Kilpatrick, Townsend & Stockton LLP

(57) ABSTRACT

The present invention relates to a malaria vaccine for administration to a host comprising an attenuated malarial parasite with a gene which has been rendered non-functional, wherein the gene, when present in naturally occurring form, encodes a protein necessary for continued in vivo survival and proliferation of the parasite and for infection of host red blood cells. The invention further relates to a malaria vaccine in which a gene that encodes a nutrient transporter protein has been rendered non-functional.

13 Claims, 6 Drawing Sheets

(3 of 6 Drawing Sheet(s) Filed in Color)

OTHER PUBLICATIONS

Gero, Annette M. et al., "Altered Purine Nucleoside Transport as a Target for Malaria Chemotherapy", *Purine and Pyrimidine Metabolism in Man VIII* 1995, 493-498.

Gero, Annette M. et al., "Purines and Pyrimidines in Malarial Parasites", *Blood Cells*, 16 1990, 467-484.

Hoffman, Stephen L. et al., "Protection of humans against malaria by immunization with radiation-attenuated *Plasmodium falciparum* sporozoites", *Journal of Infectious Diseases* Apr. 15, 2002, Chicago, IL; vol. 185(8), 1155-1164

Kirk, Kiaran "Membrane Transport in the Malaria-Infected Erythrocyte", *Physiological Reviews*, vol. 81, No. 2 Apr. 2001, 495-537.

Lambros, Chris et al., "Synchronization of *Plasmodium falciparum* Erythrocytic Stages in Culture", *J. Parasitol*, 65 (3) 1979, 418-20.

Lewis, Arthur S. et al., "Human Erythrocyte Purine Nucleoside Phosphorylase: Molecular Weight and Physical Properties", *The Journal of Biological Chemistry*, vol. 254, No. 19 Oct. 10, 1979, 9927-9932.

Mamoun, Choukri B. et al., "A set of independent selectable markers for transfection of the human malaria parasite *Plasmodium falciparum*", *Proc. Natl. Acad. Sci. USA*, vol. 96 Jul. 1999, 8716-8720.

Martin, Rowena E. et al., "The 'permeome' of the malaria parasite: an overview of the membrane transport proteins of *Plasmodium falciparum*", *Genome Biology*, vol. 6, Issue 3, Article R26 2005, R26.1-R26.22.

Menard, Robert "Medicine knockout malaria vaccine?", *Nature* Jan. 13, 2005, vol. 433(7022), 113-114.

Mueller, A. K. et al., "Genetically modified *Plasmodium* parasites as a protective experimental malaria vaccine", *Nature* Jan. 13, 2005, vol. 433(7022), 164-167.

Parker, Marie D. et al., "Identification of a nucleoside/nucleobase transporter from *Plasmodium falciparum*, a novel target for antimalarial chemotherapy", *Biochem J.* 349 2000, 67-75.

Rager, Nicolle et al., "Localization of the *Plasmodium falciparum* PfNT1 Nucleoside Transporter to the Parasite Plasma Membrane", *The Journal of Biological Chemistry*, vol. 276, No. 44 Nov. 2, 2001, 41095-41099.

Santiago, Teresa C. et al., "The *Plasmodium falciparum* PfGatp is an Endoplasmic Reticulum Membrane Protein Important for the Initial Step of Malarial Glycerolipid Synthesis", *The Journal of Biological Chemistry*, vol. 279, No. 10 Mar. 5, 2004, 9222-9232.

Sherman, Irwin W. "Biochemistry of Plasmodium (Malarial Parasites)", *Microbiological Reviews*, vol. 43, No. 4 Dec. 1979, 453-495.

Sherman, Irwin W. "Purine and Pyrimidine Metabolism of Asexual Stages", *Malaria: Parasite Biology, Pathogenesis, and Protection* 1998, 177-184.

Targett, Geoffrey et al., "Malaria vaccines 1985-2005: a full circle?", *Trends in Parasitology, Elsevier Current Trends* Nov. 1, 2005, vol. 21(11), 499-503.

Trager, William et al., "Human Malaria Parasites in Continuous Culture", *Science*, 193 Aug. 20, 1976, 673-5.

Traut, Thomas W. "Physiological concentrations of purines and pyrimidines", *Molecular and Cellular Biochemistry* 140 1994, 1-22.

Upston, Joanne M. et al., "Parasite-induced permeation of nucleosides in *Plasmodium falciparum* malaria", *Biochimica et Biophysica Acta 1236* 1995, 249-258.

Van Dijk, Melissa R. et al., "Genetically attenuated, P36p-deficient malarial sporozoites induce protective immunity and apoptosis of infected liver cells" *Proceedings of the National Academy of Sciences of the United States of America* Aug. 23, 2005, vol. 102(34), 12194-12199.

Waters, Andrew et al., "Malaria new vaccines for old?", *Cell* Feb. 24, 2006, vol. 124(4), 689-693.

Yamada, Kenneth A. et al., "Purine Metabolizing Enzymes of Plasmodium Lophurae and its Host Cell, the Duckling (Anas Domesticus) Erythrocyte", *Molecular and Biochemical Parasitology*, 2 1981, 349-358.

Chanock, Robert M. et al., "Genetic Control of the Immune Response to a *Plasmodium falciparum* Sporozoite Vaccine and to the Circumsporozoite Protein", Vaccines87 1987, 81-106, 117-124.

Crabb, B. S. et al., "Stable transgene expression in *Plasmodium falciparum*", Molecular and Biochemical Parasitology 1997, 90: 131-144.

El Bissati, Kamal et al., "Genetic evidence for the esstntial role of PfNT1 in the transport and utilization of xanthine, guanine, guanosine and adenine by *Plasmodium falciparum*", Molecular & Biochemical Parasitology 2008, 161:130-139.

Fidock, David A. et al., "Cycloguanil and Its Parent Compound Proguanil Demonstrate Distinct Activities against *Plasmodium falciparum* Malaria Parasites Transformed with Human Dihydrofolate Reductase", Molecular Pharmacology 1998, 54: 1140-1147.

Folch, Jordi et al., "A Simple Method for the Isolation and Purification of Total Lipids from Animal Tissues", The Journal of Biological Chemistry 1957, 226, 497-509.

Francis, Susan E. et al., "Biosynthesis and Maturation of the Malaria Aspartic Hemoglobinases Plasmepsins I and II", The Journal of Biological Chemistry Jun. 6, 1997, vol. 272, No. 23, 14961-14968.

Gligorijevic, Bojana et al., "Spinning Disk Confocal Microscopy of Live, Intraerythrocytic Malarial Parasites. 1. Quantification of Hemozoin Development for Drug Sensitive versus Resistant Malaria", Biochemistry 2006, 45: 12400-12410.

Gligorijevic, Bojana et al., "Stage independent chloroquine resistance and chloroquine toxicity revealed via spinning disk confocal microscopy", Molecular & Biochemical Parasitology 2008, 159: 7-23.

Holz, George G. "Lipids and the malarial parasite", Bulletin of the World Health Organization 1977, 55 (2-3): 237-248.

James, Stephanie et al., "Malaria Vaccine Development Status Report", Parasitology and International Programs Branch and Laboratory of Parasitic Diseases, National Institutes of Health 2000, 1-13.

Krishna, Sanjeev "Science, medicine, and the future. Malaria", BMJ Sep. 20, 1997, vol. 315, 730-732.

Makler, M. T. et al., "Parasite Lactate Dehydrogenase as an Assay for *Plasmodium falciparum* Drug Sensitivity", Am. J. Trop. Med. Hyg. 1993, 48(6): 739-741.

Miller, L. H. et al., "Perspectives for malaria vaccination", Phil. Trans. R. Soc. Lond. 1984, B307: 99-115.

Pessi, Gabriella et al., "A pathway for phosphatidylcholine biosynthesis in *Plasmodium falciparum* involving phosphoethanolamine methylation", PNAS Apr. 20, 2004, vol. 101, No. 16, pp. 6206-6211.

Pessi, Gabriella et al., "In Vivo Evidence for the Specificity of *Plasmodium falciparum* Phosphoethanolamine Methyltransferase and Its Coupling t othe Kennedy Pathway", The Journal of Biological Chemistry Apr. 1, 2005, vol. 280, No. 13, 12461-12466.

Pessi, Gabriiella et al., "Pathways for phosphatidylcholine biosynthesis: targets and strategies for antimalarial drugs", Future Lipidol 2006, 1(2): 173-108.

Sherman, Irwin W. "Biochemistry of Plasmodium (Malarial Parasites)", Microbiological Reviews Dec. 1979, vol. 43, No. 4, 453-495.

Vial, Henri J. et al., "Plasmodium Lipids: Metabolism and Function", Molecular Approaches to Malaria 2005, 327-352.

Witola, William H. et al., "Localization of the Phosphoethanolamine Methyltransferase of the Human Malaria Parasite *Plasmodium falciparum* to the Golgi Apparatus", The Journal of Biological Chemistry Jul. 28, 2006, vol. 281, No. 30, pp. 21305-21311.

Zeisel, Steven H. et al., "Choline: Needed for Normal Deelopment of Memory", Journal of the American College of Nutrition 2000, vol. 19, No. 5, 528S-531S.

Zeisel, Steven H. et al., "Normal plasma choline responses to ingested lecithin", Neurology Nov. 1980, 30: 1226-1229.

"Notice of Allowance" in U.S. Appl. No. 12/381,326, mailed Nov. 17, 2011.

* cited by examiner

USE OF CONDITIONAL PLASMODIUM STRAINS LACKING NUTRIENT TRANSPORTERS IN MALARIA VACCINATION

PRIOR RELATED APPLICATIONS

This application claims priority to U.S. provisional patent application Ser. No. 60/830,371 filed Jul. 11, 2006, the entire contents of which are hereby incorporated by reference.

STATEMENT AS TO FEDERALLY SUPPORTED RESEARCH

The present invention was made with United States government support under grant number AI51507 from the National Institute of Allergy and Infectious Disease and a grant from the Department of Defense. Accordingly, the United States government may have certain rights in the invention.

FIELD OF THE INVENTION

The present invention relates to the development and use of attenuated strains of malarial parasites as vaccines for the prevention and treatment of malaria. Moreover, the instant application is directed to a vaccine and methods of immunization targeted at the asexual (blood) phase of the malarial parasite's life, when the parasites are in red blood cells. Further, these attenuated strains of malaria parasites can be cultured and propagated in vitro under controlled conditions that require higher than physiological concentrations of one or more nutrients that are essential for the parasite. These attenuated strains have little if any ability to grow under in vivo conditions, such as following an injection for the purposes of vaccination.

BACKGROUND OF THE INVENTION

Status of Malaria Vaccine Development

A global public health goal is the control and eventual eradication of human malaria, which is caused primarily by one of four species of the *Plasmodium* parasite: *P. falciparum, P. vivax, P. malariae*, and *P. ovale*. It is estimated that over 500 million people in tropical regions are exposed to malaria annually, and 1.5 to 2 million people die from this disease. Efforts to control malaria have historically focused on control of the mosquito vector and the development of anti-malarial drugs. These efforts have met with only limited success. New prophylactic and therapeutic drugs are of limited effectiveness because drug-resistant strains can appear rapidly in endemic areas. Control of the mosquito vector depends largely upon implementation of insecticide-based control programs which, due to cost and other factors, are difficult to maintain in developing nations. Vector resistance to modern insecticides has compounded the problem, and resulted once again in the resurgence of malaria.

Mammalian hosts can be infected by the sporozoite form of the malaria parasite, which is injected by the female *Anopheles* mosquito during feeding. Sporozoites injected into the bloodstream are carried rapidly to the liver where they invade hepatocytes, the beginning of liver-stage infection. Once in hepatocytes, sporozoites develop into merozoite forms, which are released from hepatocytes and invade erythrocytes. Within the erythrocyte, the parasite asexually reproduces from rings to schizonts, this stage of the parasite's life cycle is known as the blood-stage. The mature schizont contains merozoites which, upon rupture of the erythrocyte, can invade other erythrocytes, causing clinical manifestations of the disease. Some merozoites differentiate into sexual forms, called gametocytes, which are taken up by mosquitoes during a blood meal. After fertilization of gametocytes in the mosquito midgut, developing ookinetes can penetrate the gut wall and encyst. Rupture of such oocysts allows release of sporozoites which migrate to the salivary glands to be injected when the female mosquito takes another blood meal, thus completing the infectious cycle. This stage, which occurs within the mosquito, is called the extrinsic cycle or mosquito stage.

Experiments conducted in the 1960s demonstrated that vaccination with X-irradiated sporozoites of *Plasmodium berghei* (*P. berghei*) protected mice against sporozoite challenge which was lethal in unvaccinated animals. This observation was later extended to clinical studies in humans, where immunization with X-irradiated sporozoites of *P. falciparum* or *P. vivax* protected human volunteers against sporozoite challenge delivered through the bites of infected mosquitoes. This protection was thought to be mediated by antibodies. Serum from immunized animals, including humans, formed a precipitate around the surface of live, mature sporozoites. This reaction has been termed the circumsporozoite precipitin (CSP) reaction. These same sera blocked the ability of sporozoites to invade human hepatoma cells in culture (ISI assay). In other studies, a single antigenic determinant localized on the surface of *P. berghei* sporozoites, termed the circumsporozoite protein, was identified. It was shown that a monoclonal antibody reacting with the circumsporozoite (CS) protein of *P. berghei* could passively transfer immunity to recipient animals. These animals were protected from sporozoite challenge in a dose-dependent fashion. Evidence also existed that cell-mediated immunity was important.

The first CS protein gene to be cloned was derived from the H strain of *P. knowlesi*, a simian parasite. The genes encoding the CS proteins of the human malaria parasites *P. falciparum, P. vivax*, the simian parasite *P. cynomolgi*, and the rodent parasite *P. berghei* were also cloned and sequenced. A characteristic feature of the CS genes of each of the parasites is a central region which encodes over one-third of the protein, containing a series of repeated peptide sequences. The primary amino acid sequence, the length of the repeated sequence, and the number of repeats vary with each species of parasite. The repeat region epitopes are characteristic of each species. The gene encoding the CS protein of *P. falciparum* specifies a central repeat region of a tetrapeptide (asn-ala-asn-pro) repeated 37 times, interrupted in four locations by the nonidentical tetrapeptide (asn-val-asp-pro). The central repeat region of *P. vivax* CS protein contains 19 nonapeptides; the central sequence of *P. knowlesi* contains 12 dodecapeptides, and the repeat region of *P. berghei* contains 12 octapeptides. Comparison of sequences from *P. knowlesi* (H strain) and *P. falciparum* and *P. vivax* reveals no sequence homology except for two short amino acid sequences flanking the repeat region, termed Region I and Region II.

Efforts to develop an effective anti-sporozoite vaccine for *P. falciparum* have used peptides derived from the circumsporozoite (CS) repeat region and the two flanking Region I and Region II sequences. These experiments showed that antibody to the repeat region but not to the conserved sequences recognized authentic CS protein, produced CSP activity, and blocked sporozoite invasion (ISI) in vitro. A recombinant DNA subunit vaccine composed of 32 *P. falciparum* tetrapeptide repeats fused to 32 amino acids of the tetracycline resistance gene was produced in *E. coli*. Likewise, a peptide-carrier vaccine composed of three repeats of the peptide asn-ala-asn-pro (NANP) conjugated to tetanus toxoid was developed. In each case, preclinical studies indicated that biologically active (as shown by CSP and ISI) anti-sporozoite antibodies were elicited as a result of immunization. Human safety and immunogenicity studies with both vaccines yielded similar results. Both vaccine preparations were well tolerated at doses ranging from 10 micrograms to 800 micrograms, and both elicited some anti-CS antibodies in all immunized subjects. However, high titers were not achieved. In addition, subsequent booster immunizations with the peptide-carrier vaccine did not result in increased antibody titers. Several individuals from each study were then challenged with live sporozoites in order to test the efficacy of these vaccine preparations. Once again, similar results were achieved with both vaccines; the level of protection (as measured by a delay in the appearance of blood stage parasites) correlated with the anti-CS antibody titers of the challenged individuals, but in each trial, only one individual was protected. Parallel studies to evaluate the feasibility of human subunit vaccine development have been examined in the rodent *P. berghei* malaria model.

Another study has reported that levels of naturally acquired antibodies to the *P. falciparum* CS protein, as high as those achieved by a subunit sporozoite vaccine, did not protect against *P. falciparum* infection during a 98-day interval in a malaria-endemic area.

In different studies, subunit vaccines containing peptides of other *P. falciparum* antigens have been investigated. In addition, recombinant vaccinia viruses which express *P. falciparum* antigens have been described for use. More current approaches to malaria vaccines also include DNA vaccines, a malaria specific protein developed using transgenic technology as a vaccine, as well as genomic and proteomic approaches.

Perspectives and advances in malaria vaccination have been described (Miller, L. H., et al., 1984, Phil. Trans. R. Soc. Lond. B307:99-115; 1985, Vaccines 87, Channock et al., eds., Cold Spring Harbor Laboratory, Cold Spring Harbor, N.Y. pp. 81-106, 117-124). More recent advances in malaria vaccines is described in a review paper by James and Miller entitled "Malaria Vaccine Development: Status Report" printed from the website of the Division of Microbiology & Infectious Diseases, National Institute of Allergy and Infectious Disease, NIH (http://www3.niaid.nih.gov/research/topics/malaria/pdf/malvacdev.pdf).

There are many scientific questions that must be addressed in the course of further development efforts on malaria vaccines. These include issues such as how to induce appropriate (protective, long-lasting, nonpathogenic) immune responses, how to structure combination vaccines, how to deal with parasite antigen diversity and antigenic variation, as well as how to deal with human genetic restriction of immune response and/or genetic predilection toward detrimental responses.

There are also a number of hurdles related to research and evaluation of candidate vaccines. These include issues regarding the appropriateness and accessibility of animal models. Other technical hurdles relate to the need to identify assays for ongoing validation of candidate antigens through process development and scale-up production, as well as assays predictive of protection for assessment of immunogenicity and efficacy in clinical trials. In addition, much careful thought must be given to clinical trial design. This is especially true for blood-stage vaccines, where the feasibility of experimental challenge infection is extremely controversial and the optimal measurement of efficacy is reduced morbidity/mortality, as well as for sexual stage vaccines, where the ultimate measurement of efficacy is interruption of malaria transmission.

The development and widespread availability of highly effective attenuated malarial vaccines to provide efficacious immunization against malaria would be highly desirable and beneficial for humans at risk of contracting the disease. No approved malaria vaccine is currently available. The drugs in present use to treat malaria are only partially effective.

SUMMARY OF THE INVENTION

The instant application is directed to vaccines and methods of immunization targeted at the asexual (blood-stage) phase of the parasite's life, when the parasites are in red blood cells. The human malaria parasite *Plasmodium falciparum* relies on the acquisition of host purines for its survival within human erythrocytes. Purine salvage by the parasite requires specialized transporters at the parasite plasma membrane (PPM), but the exact mechanism of purine entry into the infected erythrocyte and the primary purine source utilized by the parasite remain unknown. Here we report that transgenic parasites lacking the PPM transporter PfNT1 are auxotrophic for hypoxanthine, inosine and adenosine under physiological conditions and are only viable if these normally essential nutrients are provided at excess concentrations. Transport measurements across the PPM in the knockout parasite revealed a severe reduction in hypoxanthine uptake, whereas adenosine and inosine transport were only partially affected.

When injected into humans or primates, strains of *Plasmodium* lacking this essential nutrient transporter are expected to either stop growing or to undergo no more than two cycles of division due to the low availability of purines in plasma. Physiological concentrations of purines in plasma are in the range of about 0.5 µM to about 10 µM These strains could provide the basis for a safe and effective vaccine against malaria.

The present invention relates to a malaria vaccine for administration to a host wherein the vaccine comprise a malarial parasite in which at least one gene is modified and/or deleted such that the gene is non-functional, and in which the normally occurring gene encodes a protein necessary for continued in vivo survival, proliferation and infection of host red blood cells by the parasite. The species of malarial parasites includes *Plasmodium vivax, Plasmodium malaria, Plasmodium ovale* and *Plasmodium falciparum*. Strains of *P. falciparum* can include the 3D7 strain, the Vietnam-Fort (FVO) strain, Uganda-Palo Alto (FUP) strain, FCH/4 (Philippines) strain, the falciparum Santa Lucia (Salvador I) strain and the Malayan Camp (MC) strain.

The present invention also relates to malaria vaccines wherein the gene(s) of the malarial parasite that is rendered non-functional by modification or deletion normally encodes a protein necessary for nutrition of the malaria parasite, including a parasite plasma membrane transporter, such as an essential nutrient transporter (e.g., a purine transporter; a glucose transporter; an amino acid transporter, or a choline transporter).

In addition, the present invention relates to a malaria vaccine wherein the non-functional gene of the malarial parasite is rendered non-functional by knockout technology and/or homologous recombination.

In a preferred embodiment of the present invention the malaria vaccine is comprised of a malarial parasite with two genes rendered non-functional, which, in their naturally occurring state, encode two proteins necessary for the continued in vivo survival, proliferation and infection of host red blood cells by the parasite.

Another embodiment of the invention is a method for growing malarial parasites with at least one non-functional gene for use as vaccine, in which the method includes growth at non-physiological concentrations of purines or other essential nutrients. In one embodiment, parasites with a non-functional gene for a purine transporter require purine concentrations in the range of at least about 50 µM to about 2 mM in order to grow and proliferate in vitro. In another embodiment, parasites with a non-functional gene for a purine transporter require purine concentrations in the range of at least about 100 µM to about 1.5 mM in order to grow and proliferate in vitro. In a further optional embodiment, malarial parasites are isolated from the medium containing non-physiological (higher than physiological) purine concentrations and are exposed for a length of time to much lower, physiological concentrations of purines. Such exposure may confer advantages to the effectiveness and/or reliability of the resulting malaria vaccine, for example, by conferring a greater degree of control and predictability on the number of cell divisions the attenuated parasite undergoes following administration of malarial vaccine to a subject.

The malarial vaccines of the present invention can be combined with pharmaceutically acceptable carriers and immunogenic adjuvants.

Still another embodiment of the present invention relates to a method of eliciting an immune response in a host comprising introducing into the host any one of the malaria vaccines mentioned above in an amount sufficient to elicit an immune response. In a preferred embodiment the host is a human and the vaccine is administered by injection.

In yet another embodiment, the present invention relates to a method of immunizing a host comprising introducing into the host any one of the malaria vaccines mentioned above in an amount sufficient to immunize the host against malaria. In a preferred embodiment the host is a human and the vaccine is administered by injection.

In another embodiment, the present invention relates to a kit for immunizing an animal against malaria comprising a malarial parasite with at least one gene which has been rendered non-functional, wherein the non-functional gene, when present in naturally occurring form, encodes a protein necessary for continued in vivo survival, proliferation, and infection of host red blood cells by the parasite.

In a further embodiment, the invention relates to a method for immunizing an animal against malaria comprising preparing a malarial parasite, wherein the malarial parasite comprises at least one gene rendered non-functional, wherein the non-functional gene, when present in naturally occurring form, encodes a protein necessary for continued in vivo survival, proliferation, and infection of host red blood cells by the parasite; growing and propagating the resulting attenuated malarial parasite using a growth medium comprising a higher than physiological concentration of one or more essential nutrients; isolating the attenuated parasite from the growth medium; and, administering the attenuated parasite in an amount sufficient to elicit an immune response in the animal.

In addition, the instant invention also relates to a live *Plasmodium* organism that is genetically engineered to render a blood-stage-specific gene non-functional, wherein the non-functional gene, when present in naturally occurring form, encodes a protein necessary for continued in vivo survival, proliferation, and infection of host red blood cells by the parasite.

In a further embodiment, the present invention discloses a method for inoculating a vertebrate host against malaria, by administering to the host a live *Plasmodium* organism that is genetically engineered to render a blood-stage-specific gene non-functional.

In another embodiment, the present invention relates to a vaccine composition comprising a live *Plasmodium* organism that is genetically engineered to render a blood-stage-specific gene non-functional.

Further, the present invention is directed to a use as a malaria vaccine of a live *Plasmodium* organism that is genetically engineered to render a blood-stage-specific gene non-functional.

In another embodiment, the present invention relates to a method of producing a vaccine composition, by suspending in a pharmaceutically acceptable carrier solution a live *Plasmodium* organism that is genetically engineered to render a blood-stage-specific gene non-functional.

Other embodiments and advantages of the invention are set forth in part in the description which follows, and will be obvious from this description, or may be learned from the practice of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
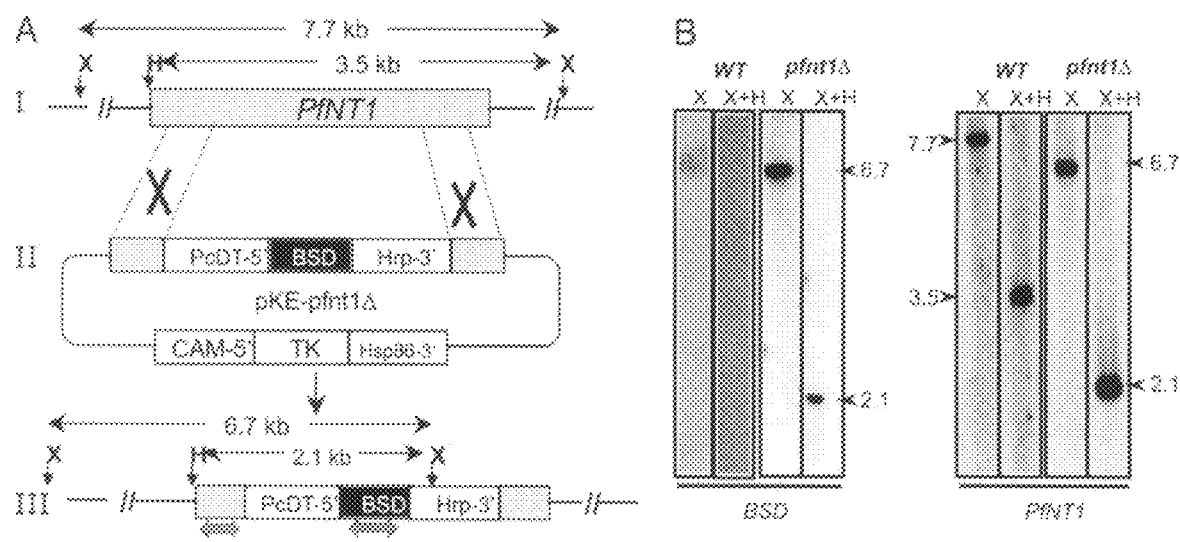
FIG. 1 illustrates the strategy for PfNT1 disruption by double cross-over; (A) Gene disruption strategy. I: schematic representation of wild-type PfNT1 chromosomal locus; II: the plasmid vector pKEΔPfNT1 used for stable transformation of *P. falciparum*; and III: the proposed model of integration of the plasmid by double cross-over into PfNT1 chromosomal locus. (B) Southern blot analysis of XbaI (X) and XbaI+HindIII (X-H) digested genomic DNA from WT and pfnt1Δ parasites using BSD- and PfNT1-specific probes (indicated by gray right-left arrows).

Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein.

Nutrient Requirements of Malarial Parasites

As mentioned above, malaria is one of the foremost threats to human health in the tropical regions of the world (*World Health Organ Tech Rep Ser* (2000) 892, i-v, 1-74). The disease is especially challenging to treat because of the widespread emergence of drug-resistant parasites and the limited number of available antimalarial drugs. As a consequence, better antimalarial therapies are urgently needed. *Plasmodium falciparum*, the causative agent of the most deadly form of human malaria, exhibits a complex life cycle that involves both an invertebrate vector, the *Anopheles* mosquito, and humans. While the ability of the parasite to invade human red blood cells (RBCs) provides it with an ideal refuge from immune attacks during the blood-stage of infection, RBCs are deficient in various nutrients required for parasite survival and multiplication. Therefore, the parasite has evolved novel transport machineries and specialized enzymes to acquire and metabolize host nutrients. Perhaps most striking is the nutritional requirement for purines. Unlike mammalian cells which synthesize purines de novo, *P. falciparum* is incapable of purine biosynthesis and has consequently evolved a unique complement of purine salvage enzymes that enables the parasite to scavenge host purines (Gero, A. M. & O'Sullivan, W. J. (1990) *Blood Cells* 16, 467-84; discussion 485-98; Sherman, I. (1998) in *Malaria: Parasite Biology, Biogenesis, Protection*, ed. Sherman, I., Ed (American Association of Microbiology Press, pp. 177-184; and Sherman, I. W. (1979) *Microbiol Rev* 43, 453-95). The first step of purine acquisition entails the uptake of purines from the host milieu. Because of the essential function of purine salvage in parasite growth and multiplication, purine transporters are regarded as ideal targets for the development of novel therapeutic strategies to combat malaria (Gero, A. M. & Upston, J. M. (1994) *Adv Exp Med Biol* 370, 493-8).

While it is known that purine transport across the PPM requires specialized purine transporters (Upston, J. M. & Gero, A. M. (1995) *Biochim Biophys Acta* 1236, 249-58), the pathways of purine translocation between the intracellular parasite and the host environment are unknown. Uninfected RBCs express a high affinity, equilibrative nucleoside transporter, hENT1, that mediates the sodium-independent uptake of a broad spectrum of purine and pyrimidine nucleosides (Boleti, H., Coe, I. R., Baldwin, S. A., Young, J. D. & Cass, C. E. (1997) *Neuropharmacology* 36, 1167-79). RBCs also harbor adenosine deaminase (ADA) and purine nucleoside phosphorylase (PNP) enzymes, which convert adenosine and inosine into hypoxanthine. However, the role of host transporters and enzymes in purine salvage by the parasite remains unknown. Furthermore, it is not known whether intraerythrocytic *P. falciparum* salvage a full complement of purine nucleosides and nucleobases from the RBC cytosol or solely hypoxanthine. Recently, PfNT1 was the first purine transporter to be identified and functionally characterized at the molecular level in *Plasmodium* (Carter, N. S., Ben Mamoun, C., Liu, W., Silva, E. O., Landfear, S. M., Goldberg, D. E. & Ullman, B. (2000) *J Biol Chem* 275, 10683-91; Rager, N., Mamoun, C. B., Carter, N. S., Goldberg, D. E. & Ullman, B. (2001) *J Biol Chem* 276, 41095-9; and Parker, M. D., Hyde, R. J., Yao, S. Y., McRobert, L., Cass, C. E., Young, J. D., McConkey, G. A. & Baldwin, S. A. (2000) *Biochem J* 349, 67-75). PfNT1 shares sequence and topological similarities to well-characterized transporters of the eukaryotic equilibrative nucleoside transporter family. However, the primary sequence of PfNT1, its substrate specificity, kinetic properties and inhibition profile are sufficiently different from hENT1, to suggest that if PfNT1 plays an essential function in *P. falciparum* development and multiplication it could be an excellent drug target.

Expression studies in *Xenopus laevis* oocytes revealed that PfNT1 has a broad ligand specificity for D- and L-nucleosides as well as for nucleobases (Carter, N. S., Ben Mamoun, C., Liu, W., Silva, E. O., Landfear, S. M., Goldberg, D. E. & Ullman, B. (2000) *J Biol Chem* 275, 10683-91; Rager, N., Mamoun, C. B., Carter, N. S., Goldberg, D. E. & Ullman, B. (2001) *J Biol Chem* 276, 41095-9; and Parker, M. D., Hyde, R. J., Yao, S. Y., McRobert, L., Cass, C. E., Young, J. D., McConkey, G. A. & Baldwin, S. A. (2000) *Biochem J* 349, 67-75), such as purines and pyrimidines. In this heterologous transport system, Carter and colleagues showed that PfNT1 has a high affinity for adenosine (Carter, N. S., Ben Mamoun, C., Liu, W., Silva, E. O., Landfear, S. M., Goldberg, D. E. & Ullman, B. (2000) *J Biol Chem* 275, 10683-91) and provided indirect evidence that hypoxanthine was not a high affinity ligand (unpublished data), whereas Parker and colleagues found that PfNT1 has a low affinity for both adenosine and hypoxanthine (Parker, M. D., Hyde, R. J., Yao, S. Y., McRobert, L., Cass, C. E., Young, J. D., McConkey, G. A. & Baldwin, S. A. (2000) *Biochem J* 349, 67-75). Subsequent studies with infected-RBCs revealed that PfNT1 is localized to the parasite plasma membrane (PPM) and expressed throughout the intraerythrocytic life cycle but is maximally expressed prior to parasite schizogony at the peak of nucleic acid utilization (Rager, N., Mamoun, C. B., Carter, N. S., Goldberg, D. E. & Ullman, B. (2001) *J Biol Chem,* 276, 41095-9). Since the initial characterization of PfNT1, three other putative equilibrative nucleoside transporters, designated PfNT2, PfNT3 and PfNT4, have been identified within the *P. falciparum* genome. However, as yet these have not been functionally authenticated and thus, their contribution to parasite purine acquisition remains undetermined.

The ability to create a conditionally lethal pfnt1Δ mutant in *P. falciparum* establishes that PfNT1 is absolutely required for purine acquisition by *P. falciparum* under physiological circumstances. *P. falciparum* cannot synthesize purine nucleotides de novo and obligatorily depend upon purine salvage from the host for their synthesis of nucleotides and nucleic acids, and consequently for their ability to proliferate and cause disease. The loss of PfNT1 activity results in inhibition of parasite growth under physiological conditions under which concentrations of salvageable purines have been reported to be between 0.4-6 µM (Traut, T. W. (1994) *Mol Cell Biochem,* 140, 1-22). This growth defect can be suppressed by the addition of excessive, non-physiological levels of hypoxanthine, adenosine, or inosine, thus enabling purine acquisition by some additional but unknown mechanism and pharmacologically circumventing the genetic consequences of the conditionally lethal mutation.

The Role of PfNT1 in Hypoxanthine Uptake Across the PPM

Figure 6:
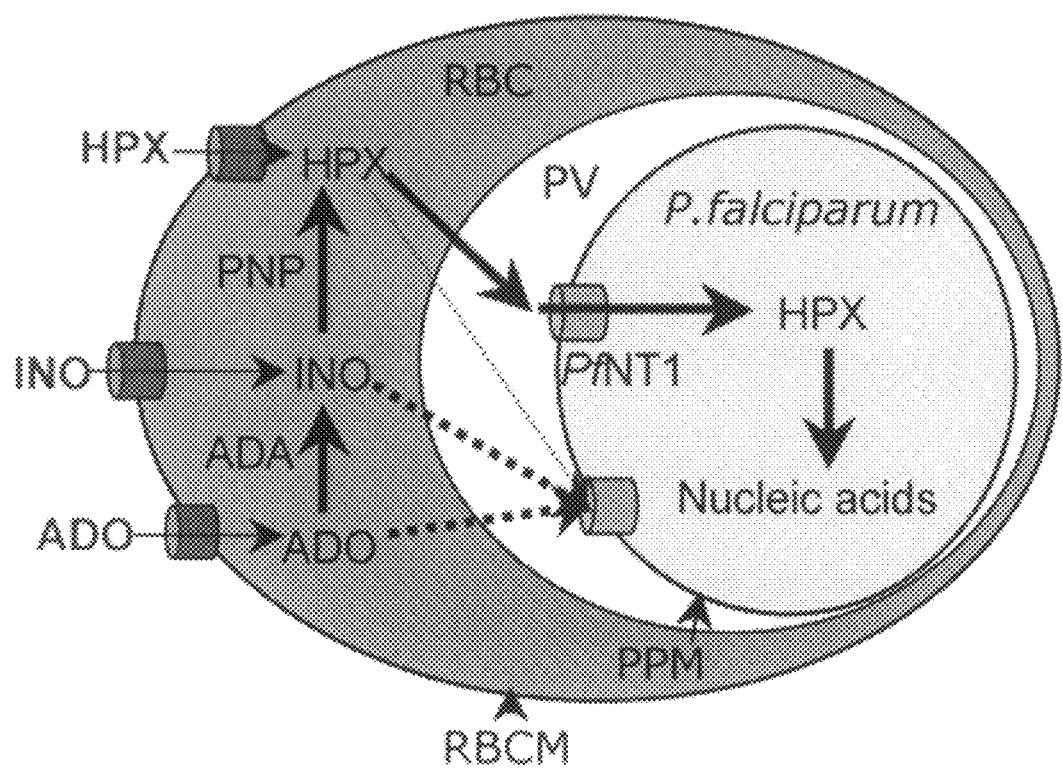
FIG. 6 illustrates a model for sequential purine uptake pathways in *P. falciparum*-infected erythrocytes; Hypoxanthine (HPX), adenosine (ADO) and inosine (INO) are transported into the red blood cell (RBC) cytoplasm via endogenous purine transporters. Inside the erythrocyte cytoplasm, adenosine and inosine are first converted into hypoxanthine before being transported along with transported hypoxanthine across the parasite plasma membrane (PPM) into the parasite cytoplasm; Alternative routes for entry of adenosine and inosine are represented in dotted lines. These additional transporters are unlikely to play an important role under physiological conditions. Guanine uptake into the parasite relies solely on PfNT1; PNP: purine nucleoside phosphorylase; ADA: adenosine deaminase; PV: parasitophorous vacuole; RBCM: red blood cell membrane.

Purine transporters have been identified in several parasitic protozoa and their biochemical properties and sensitivities to inhibitors have been determined in a number of heterologous expression systems within null backgrounds (Carter, N. S., Landfear, S. M. & Ullman, B. (2001) *Trends Parasitol,* 17, 142-5). Using a parallel approach, PfNT1 was shown to have a relatively high affinity for adenosine and a lower affinity for inosine and hypoxanthine (Carter, N. S., Ben Mamoun, C., Liu, W., Silva, E. O., Landfear, S. M., Goldberg, D. E. & Ullman, B. (2000) *J Biol Chem,* 275, 10683-91; Parker, M. D., Hyde, R. J., Yao, S. Y., McRobert, L., Cass, C. E., Young, J. D., McConkey, G. A. & Baldwin, S. A. (2000) *Biochem J,* 349, 67-75). Interestingly, pfnt1Δ parasites were non-viable at physiological concentrations of hypoxanthine, adenosine or inosine and exhibited relatively normal intraerythrocytic cycle only at higher concentrations of these substrates. These results demonstrated that under physiological conditions, PfNT1 is essential for hypoxanthine, adenosine and inosine uptake into the parasite, and that at higher concentrations these substrates could be transported via a secondary mechanism. The ability of RBC-liberated pfnt1Δ parasites to effectively transport adenosine and inosine demonstrates that the PPM harbors one or more additional permeases capable of transporting these nucleosides. Because nutrient limitation studies verified that adenosine and inosine do not support growth of the pfnt1Δ mutant at physiological concentrations, these data imply that these nucleosides do not reach the PPM membrane in their native form. Rather, adenosine and inosine are converted in the RBC cytoplasm into a PfNT1 substrate (FIG. 6). Hypoxanthine is the most likely candidate for this substrate, since RBCs are known to express high levels of both adenosine deaminase and purine nucleoside phosphorylase activities (Daddona, P. E. & Kelley, W. N. (1977) *J Biol Chem,* 252, 110-5; Lewis, A. S. & Lowy, B. A. (1979) *J Biol Chem,* 254, 9927-32), which sequentially metabolize adenosine to inosine and then to hypoxanthine. This hypothesis is supported by the fact that *P. falciparum*-infected RBCs are capable of converting radiolabeled adenosine into hypoxanthine in the RBC cytoplasm and subsequently, radiolabeled hypoxanthine could be detected in the parasite cytoplasm (Yamada, K. A. & Sherman, I. W. (1981) *Mol Biochem Parasitol,* 2, 349-58; Sherman, I. (1998) *Malaria, Parasite Biology, pathogenesis and Protection* (ASM Press, Washington D.C.)).

Nutrient Uptake into *P. falciparum* is Sequential

In the past 30 years, three models have been proposed to account for the movement of nutrients between the host and the intracellular parasite (Kirk, K. (2001) *Physiol Rev,* 81, 495-537). In the first model, referred to as the "sequential pathway," nutrients are first transported across the RBC membrane into the erythrocyte cytoplasm, and then translocated into the parasite after crossing the parasitophorous vacuolar membrane (PVM) and the PPM using specialized PPM transporters. In the second model, referred to as the "endocytosis model", nutrients are first transported across the RBC membrane into the erythrocyte cytoplasm and then progress into the parasite by endocytosis. The third model involves specialized entry mechanisms, referred to as the "parallel pathways," that allow direct movement of nutrients between the host medium and the parasite without entering the erythrocyte cytoplasm. These results strongly support a sequential pathway mechanism for entry of exogenous purines into *P. falciparum* (FIG. 6), because the parasite harbors additional pathways capable of transporting adenosine and inosine, although at physiological concentrations these purines are not capable of supporting the growth of knockout parasites. This supports the conjecture that these nucleosides do not gain direct access to the parasite and that they require prior conversion into hypoxanthine, reactions that occur within the RBC cytoplasm.

The Role of Other Permeases in Malarial Purine Uptake

Growth of pfnt1Δ could be maintained only at high concentrations of hypoxanthine, adenosine or inosine. Furthermore, transport studies in free-parasites revealed that the PPM harbors additional mechanisms capable of transporting adenosine or inosine. The completed genome sequence of *P. falciparum* revealed three nucleoside permease candidates, all members of the equilibrative nucleoside transporter family, for purine permeases (Martin, R. E., Henry, R. I., Abbey, J. L., Clements, J. D. & Kirk, K. (2005) *Genome Biol,* 6, R26). Whether these putative permeases are capable of recognizing and transporting nucleosides and whether they are expressed at the PPM await further investigation. The results, however, suggest that additional PPM permeases are unlikely to play an important role in parasite intraerythrocytic development, that PfNT1 is the major route of purine uptake under physiological conditions, and that PfNT1 is essential for intraerythrocytic parasite development.

The conditional lethality of the pfnt1Δ mutation in *P. falciparum* establishes that PfNT1 is absolutely indispensable for purine acquisition by *P. falciparum* under physiological purine conditions and that PfNT1 is the major route for purine salvage. This study also substantiates that erythrocyte enzymes convert exogenous adenosine and inosine to hypoxanthine prior to translocation into the parasite by PfNT1. Although PfNT1 shares sequence and topological similarities with hENT1 (human equilibrative nucleoside transporter 1) the major nucleoside transporter in human cells including erythrocytes, PfNT1's ligand specificity, kinetic parameters, and inhibition profile are all sufficiently different from hENT1 to make it an attractive target for selective therapeutic drug design.

EMBODIMENTS OF THE INVENTION

The present invention relates to the development and use of attenuated strains of malarial parasites as vaccines for the prevention and treatment of malaria. Moreover, the instant application is directed to a vaccine and methods of immunization targeted at the asexual (blood) phase of the malarial parasite's life, when the parasites are in red blood cells. The present invention relates to a malaria vaccine for administration to a host comprising a malarial parasite with at least one non-functional gene which encodes a protein necessary for continued in vivo survival, proliferation and infection of host red blood cells by the parasite. The species of malarial parasites can include *Plasmodium vivax, Plasmodium malariae, Plasmodium ovale* and *Plasmodium falciparum*. Strains of *P. falciparum* can include the 3D7 strain, the Vietnam-Fort (FVO) strain, Uganda-Palo Alto (FUP) strain, FCH/4 (Philippines) strain, the falciparum Santa Lucia (Salvador I) strain and the Malayan Camp (MC) strain.

The present invention also relates to malaria vaccines wherein a gene of the malarial parasite is rendered non-functional in which the gene, in its naturally occurring state, encodes a protein necessary for nutrition of the malaria parasite, including parasite plasma membrane transporter, such as an essential nutrient transporter (e.g., a nucleoside transporter, in particular a purine transporter; a glucose transporter; an amino acid transporter). In the description herein, a gene which has been rendered non-functional by any method is sometimes referred to as a "non-functional gene."

In addition, the present invention relates to a malaria vaccine wherein the non-functional gene of the malarial parasite is rendered non-functional by knockout technology and/or homologous recombination.

In a preferred embodiment of the present invention the malaria vaccine is comprised of a malarial parasite with two non-functional genes, which encode two proteins necessary for continued in vivo survival, proliferation and infection of host red blood cells by the parasite.

The malarial vaccines of the present invention can be combined with pharmaceutically acceptable carriers and immunogenic adjuvants.

Still another embodiment of the present invention relates to a method of eliciting an immune response in a host comprising introducing into the host any one of the malaria vaccines mentioned above in an amount sufficient to elicit an immune response. In a preferred embodiment the host is a human and the vaccine is administered by injection.

DEFINITIONS

In the description that follows, a number of terms used in recombinant DNA, parasitology and immunology are extensively utilized. In order to provide a clear and consistent understanding of the specification and claims, including the scope to be given such terms, the following definitions are provided.

The term 'eliciting an immune response' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent.

A 'vaccine' is an immunogenic composition, such as an attenuated parasite strain, capable of eliciting protection against malaria, whether partial or complete. A vaccine may also be useful for treatment of an infected individual, in which case it is called a therapeutic vaccine.

The term 'therapeutic' refers to a composition capable of treating malaria infection.

The term 'effective amount' for a therapeutic or prophylactic treatment refers to an amount of a malarial parasite of the present invention sufficient to induce an immunogenic response in the individual to which it is administered. Preferably, the effective amount is sufficient to effect prevention or to effect treatment, as defined above. In a preferred embodiment, an effective amount of vaccine is directed to, or effective against, the blood-stage of malaria infection. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of numbers of malarial parasites for prophylaxis of malaria disease are about 10 to 1,000,000; most preferably about 10,000 to 50,000 dose. Several doses of vaccine may be needed per individual in order to achieve a sufficient immune response and subsequent protection against malaria.

In general, an 'epitope' is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type (group)-specific variants, e.g., of the currently known sequences or strains belonging to *Plasmodium* such as 3D7, FVO and MC, or any other known or newly defined *Plasmodium* strain.

The term 'nucleobase' includes purines and pyrimidines.
Malarial Species and Strains Malarial species relating to the present invention include *Plasmodium vivax, Plasmodium malariae, Plasmodium ovale* and *Plasmodium falciparum*. Particular strains of *P. falciparum* related to the present invention include the 3D7 strain, the Vietnam-Fort (FVO) strain, the Uganda-Palo Alto (FUP) strain, the FCH/4 (Philippines) strain, the falciparum Santa Lucia (Salvador I) strain and the Malayan Camp (MC) strain. Other *Plasmodium* species parasitize birds and non-human animals.
Nutrient Transporters Genes for nutrient transporters that are related to the present invention and that are useful when made non-functional include genes for any transporters that are involved in the uptake of essential nutrients from human serum into malaria parasites when such parasites are present inside infected erythrocytes (blood-stage). Among these transporters are the purine transporter; the glucose transporter; amino acid transporter and the choline transporter.

Knockout Technology

An important aspect of the present invention is a null mutation in the genes relating to the nutrition of malarial parasites. One method of inhibiting the expression of these genes is to disrupt the gene in malarial parasite cells. This method is generally known as knockout technology.

In a general sense, preparation of a knockout requires first introducing a nucleic acid construct that will be used to suppress expression of a particular gene into a malarial parasite cell, where it is to be integrated into the parasite's genome at the appropriate location.

U.S. Pat. No. 5,616,491, incorporated herein by reference in its entirety, generally describes the techniques involved in the preparation of knockout genes. The term "knockout" refers to a partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of: (1) DNA from some portion of the gene (exon sequence, intron sequence, and/or promoter sequence) to be suppressed; and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA).

The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into malarial parasite cell and is integrated into the cell genomic DNA, usually by the process of homologous recombination.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

Usually, the DNA to be used in the knockout construct will be one or more exon and/or intron regions, and/or a promoter region from the genomic sequence provided herein, but may also be cDNA sequence. Generally, the DNA will be at least about 500 bp (base pairs) to 1 kilobase (kb) in length, and in certain aspects up to 3-4 kb in length, thereby providing sufficient complementary sequence for hybridization when the knockout construct is introduced into the genomic DNA of the cell.

Preparation and Formulation of Malarial Vaccines

As described herein, the attenuated malarial strains may be introduced into a host by injection or other routes of administration, in one or more administration events at different time points, thereby eliciting an immune response protective against malarial infection. In a further embodiment, the attenuated malarial strains and formulations employing the strains may be admixed in various combinations and or admixed with other known proteins, peptides, or adjuvants which are known or believed to facilitate an immunological response, thereby providing enhanced immunity. In an alternative embodiment, the components of the present invention may be administered separately, i.e., at different time points, which is known or believed to facilitate an immunological response, thereby providing protection against malarial infection. For example, the attenuated strain of the present invention can be combined with one or more antigens or toxoids, such as tetanus toxoid, diphtheria toxoid, cholera toxoid, ovalbumin (OVA), or keyhole limpet haemocyanin (KLH).

The pharmaceutically acceptable carriers which can be used in the present invention include, but are not limited to, an excipient, a stabilizer, a binder, a lubricant, a colorant, a disintegrant, a buffer, an isotonic agent, a preservative, an anesthetic, and the like which are commonly used in a medical field.

Also, the dosage form, such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like, can be used appropriately depending on the administration method and the polypeptides of the present invention can be accordingly formulated. Pharmaceutical formulations are generally known in the art and are described, for example, in Chapter 25.2 of Comprehensive Medicinal Chemistry, Volume 5, Editor Hansch et al, Pergamon Press 1990.

The present invention also provides compositions containing the attenuated strains thereof and one or more suitable adjuvants commonly used in the field of immunology and medicine to enhance the immune response in a subject. Examples of such adjuvants include monophosphoryl lipid A (MPL), a detoxified derivative of the lipopolysaccharide (LPS) moiety of *Salmonella* Minnesota R595, which has retained immunostimulatory activities and has been shown to promote Th1 responses when co-administered with antigens (see U.S. Pat. No. 4,877,611; Tomai et al., *Journal of Biological Response Modifiers*, (1987), 6:99-107; Chen et al., *Journal of Leukocyte Biology*, (1991), 49:416-422; Garg & Subbarao, *Infection and Immunity*, (1992), 60(6):2329-2336; Chase et al., *Infection and Immunity*, (1986), 53(3):711-712; Masihi et al, *Journal of Biological Response Modifiers*, (1988), 7:535-539; Fitzgerald, *Vaccine*, (1991), 9:265-272; Bennett et al, *Journal of Biological Response Modifiers* (1988), 7:65-76; Kovach et al., *Journal of Experimental Medicine*, (1990), 172:77-84; Elliott et al., *Journal of Immunology*, (1991), 10:69-74; Wheeler A. W., Marshall J. S., Ulrich J. T., *International Archives of Allergy and Immunology*, (2001), 126(2):135-9; and Odean et al., *Infection and Immunity*, (1990), 58(2):427432); MPL derivatives (see U.S. Pat. No. 4,987,237) other general adjuvants (see U.S. Pat. No. 4,877,611); CpG and ISS oligodeoxynucleotides (see U.S. Pat. No. 6,194,388; U.S. Pat. No. 6,207,646; U.S. Pat. No.

6,239,116; U.S. Pat. No. 6,339,068; McCluskie, M. J., and H. L. Davis. Vaccine 2002. 19:413422; Ronaghy A, Prakken B J, Takabayashi K, Firestein G S, Boyle D, Zvailfler N J, Roord S T, Albani S, Carson D A, Raz E. Immunostimulatory DNA sequences influence the course of adjuvant arthritis. *Journal of Immunology*, (2002), 168(1):51-6; Miconnet et al (2002) 168(3) *Journal of Immunology* pp 1212-1218; Li et al (2001) *Vaccine*, 20(1-2):148-157; Davis (2000) *Developmental Biology* 104:165-169; Derek T. O'Hagan, Mary Lee MacKichan, Manmohan Singh, Recent developments in adjuvants for vaccines against infectious diseases, Biomolecular Engineering 18 (3) (2001) pp. 69-85; McCluskie et al (2001) Critical Reviews in Immunology 21(1-3):103-120); trehalose dimycolate (see U.S. Pat. No. 4,579,945); amphipathic and surface active agents, e.g., saponin and derivatives such as QS21 (see U.S. Pat. No. 5,583,112); oligonucleotides (Yamamoto et al, *Japanese Journal of Cancer Research*, 79:866-873, 1988); detoxified endotoxins (see U.S. Pat. No. 4,866,034); detoxified endotoxins combined with other adjuvants (see U.S. Pat. No. 4,435,386); combinations with QS-21 (see U.S. Pat. No. 6,146,632); combinations of detoxified endotoxins with trehalose dimycolate and endotoxic glycolipids (see U.S. Pat. No. 4,505,899); combinations of detoxified endotoxins with cell wall skeleton (CWS) or CWS and trehalose dimycolate (see U.S. Pat. Nos. 4,436,727, 4,436,728 and 4,505,900); combinations of just CWS and trehalose dimycolate, without detoxified endotoxins (as described in U.S. Pat. No. 4,520,019); chitosan adjuvants (see U.S. Pat. Nos. 5,912,000; 5,965,144; 5,980,912; Seferian, P. G., and Martinez, M. L. Immune stimulating activity of two new chitosan containing adjuvant formulations (2001) *Vaccine*, (2000), 19(6):661-8). All of the references cited in this paragraph are incorporated herein by reference.

In another embodiment, various adjuvants, even those that are not commonly used in humans, may be employed in animals where, for example, one desires to subsequently obtain activated T cells or to protect valuable or valued animals from infection due to malarial infections.

Administration of Vaccines

As used herein the subject that would benefit from the administration of the attenuated vaccines and formulations described herein include any host that can benefit from protection against malarial infection. In a preferred embodiment, the subject is a human. In a second embodiment, the subject is a domestic animal, including but not limited to dog, cat, horse, bovine (meaning any sex or variety of cattle) or other such domestic animals. In another embodiment, the subject is a non-human primate or an animal known to be or proposed to be an animal model of human malarial infection.

By providing an attenuated vaccine capable of eliciting an immune response in a subject human, including vaccination, the invention covers any strain of *Plasmodium* incapable of conversion to the parasitic, disease-causing virulent phase but that induces an immune reaction that results in or augments the subject's level of immune protection against malarial infection.

As used herein, "inhibit", "inhibiting" or "inhibition" includes any measurable or reproducible reduction in the infectivity of a malarial strain in the subject host. "Reduction in infectivity" means the ability of the subject to prevent or limit the spread of the malarial strain in red blood cells and tissues or organs exposed or infected by said malarial parasite. Furthermore, "amelioration", "protection", "prevention" and "treatment" mean any measurable or reproducible reduction, prevention, or removal of any of the symptoms associated with malarial infectivity, and particularly, the prevention, or amelioration of *P. falciparum* infection and resultant pathology itself.

The dosages of the attenuated vaccines used to provide immunostimulation include from about 10 to 1,000,000 malarial parasite cells, inclusive of all ranges and subranges there between. Such amount may be administered as a single dosage or may be administered according to a regimen, including subsequent booster doses, whereby it is effective; e.g., the compositions of the present invention can be administered one time or serially over the course of a period of days, weeks, months and or years.

The compositions of the attenuated vaccines can be administered by any suitable administration method including, but not limited to, injections (subcutaneous, intramuscular, intracutaneous, intravenous, intraperitoneal), oral administration, intranasal administration, inhalation, or other methods of instillation known in the art.

Kits

Also included within the scope of the present invention are kits suitable for providing compositions of the attenuated vaccines. For example, in such a kit one vial can comprise the attenuated malarial strain of the invention admixed with a pharmaceutically acceptable carrier, either in a aqueous, non-aqueous, or dry state; and a second vial which can carry immunostimulatory agents, and or a suitable diluent for the composition, which will provide the user with the appropriate concentration of malarial parasite to be delivered to the host. In one embodiment, the kit will contain instructions for using the composition and other components, as included; such instructions can be in the form of printed, electronic, visual, and or audio instructions. The vaccinations will normally be at from two to twelve week intervals, more usually from three to five week intervals. Periodic boosters at intervals of 1-5 years, usually three years, will be desirable to maintain protective levels. The course of the immunization may be followed by assays for activated T cells produced, skin-test reactivity, or other indicators of an immune response to a malarial strain.

Having generally described the attenuated strains of malarial strains useful as vaccines and the methods to create and administer them to elicit protective immune responses, a further understanding can be obtained by reference to certain specific examples that are provided herein for purposes of illustration only, and are not intended to be limiting unless otherwise specified.

All publications and patent applications cited in this specification are herein incorporated by reference as if each individual publication or patent application were specifically and individually indicated to be incorporated by reference in their entirety.

EXAMPLES

Materials and Methods

Construction of Transfection Plasmids

To construct the targeting vector pRZ/TK/PfNT1.5'-BSD-PfNT1.3' for PfNT1 disruption, a 482 bp fragment (nucleotides 50-532 of the ORF) of PfNT1 was amplified by PCR and subcloned into the HindIII/BlpI site upstream of the PcDT promoter in the pRZ-TK-BSD2 vector. This plasmid encompasses the positive selectable marker blasticidin-s-deaminase (BSD) (Mamoun, C. B., Gluzman, I. Y., Goyard, S., Beverley, S. M. & Goldberg, D. E. (1999) *Proc Natl Acad Sci USA*, 96, 8716-20) from *Aspergillus terreus* that confers resistance to blasticidin and whose expression in *P. falci-*

*parum* is under the regulatory control of the *P. Chabaudi* DHFR/TS promoter and the negative marker thymidine kinase (TK) from Herpes simplex that confers sensitivity to ganciclovir and whose expression is under the regulatory control of the *P. falciparum* CAM promoter. A second PCR was used to amplify a 482 bp fragment (nucleotides 772-1255 of the ORF) of PfNT1 for directional cloning at the EcoRI site downstream of the HrpII terminator in the pRZ-TK-BSD2 vector.

Disruption of the PfNT1 Locus

Packed *P. falciparum* strain 3D7 infected human RBCs (100 μl) were mixed with ~100 μg of plasmid DNA in 400 μl of cytomix and electroporated at 0.31 kV and 950 μF in a 0.2-cm cuvette using a Gene Pulser II (Bio-Rad). After 48 h, 2.5 μg/ml blasticidin was added. Blasticidin-resistant parasites were observed after 3 weeks. To eliminate parasites containing episomes, Ganciclovir, a subversive substrate of the TK enzyme, was applied for an additional three weeks. Surviving parasites were cloned by limiting dilution. Note that parasites were cultured as described (Trager, W. & Jensen, J. B. (1976) Science, 193, 673-5), except that 1.5 mM hypoxanthine was added to the medium for transfectants.

Southern Hybridization of the Disrupted PfNT1 Locus

Ten micrograms of genomic DNA from wild-type and pfnt1Δ parasites was digested with Xba I and Hind III, separated on a 0.8% agarose gel, and transferred to positively charged nylon membrane (Roche Molecular Biochemicals). Membranes were probed with [α-$^{32}$P]dCTP-labeled PfNT1 and BSD probes.

Western Blot Analysis

Western analysis was performed as described (Rager, N., Mamoun, C. B., Carter, N. S., Goldberg, D. E. & Ullman, B. (2001) *J Biol Chem*, 276, 41095-9; Santiago, T. C., Zufferey, R., Mehra, R. S., Coleman, R. A. & Ben Mamoun, C. (2004) *J Biol Chem*, 279, 9222-32) on protein extracts from asynchronous cultures of wild-type and pfnt1Δ strains. Blots were probed with affinity-purified antibodies to PfNT1 (1:1000) and glycerol-3-phosphate acyltransferase, PfGat (1:1000), a marker which served as a loading control.

Microscopy

To determine parasite life cycle stage, infected-RBCs were Giemsa-stained and analyzed by bright-field microscopy. For immunofluorescence microscopy, asynchronous cultures of *P. falciparum* were prepared essentially as previously described (Rager, N., Mamoun, C. B., Carter, N. S., Goldberg, D. E. & Ullman, B. (2001) *J Biol Chem*, 276, 41095-9). Coverslips were incubated at room temperature with gentle shaking for 1 h with both affinity-purified PfNT1 antibodies at a concentration of 1:500 (Rager) and mouse monoclonal antibodies to erythrocyte Band 3 protein from Sigma, which were used at a concentration of 1:500. The coverslips were washed to remove excess antibody and incubated with anti-rabbit antibody conjugated to fluorescein isothiocyanate (FITC) and anti-mouse secondary antibody conjugated to Texas red dye (Molecular Probes) for 1 h at room temperature to visualize the PfNT1 and Band 3 antibodies. Nuclei were stained by incubating the coverslips in PBS containing 3 μg/ml of Hoechst stain (Molecular Probes) for 5 min at room temperature. The coverslips were washed and then mounted on slides with Antifade (Molecular Probes) and images analyzed by high-resolution fluorescence using deconvolution protocols. Microscopy was performed with a Nikon eclipse TE2000-E microscope using filter 96320/HYQ (ex. 480-440/em. 440) for FITC, 96312/G2EC (ex. 540-525/em. 620-660) for Rhodamine, and 96310/UV2EC (ex. 360-340/em. 460-450) for DAPI.

Parasite Lactate Dehydrogenase Assay for Detecting Parasites

The reagents for the parasite LDH assay, 3-acetylpyridine adenine dinucleotide (APAD), nitroblue tetrozolium (NBT), and Diaphorase, were obtained from Sigma-Aldrich (St. Louis, Mo.). The malstat reagent was prepared by mixing 13 mg/ml of Tris-Cl pH 9.0, 20 mg/ml of lithium L-lactate, 0.66 mg/ml of 3-acetylpyridine NAD (APAD), and 0.2% Triton X-100. To perform the pLDH assay, 20 μl of infected RBCs were mixed with 10 μl of 1 mg/ml diaphorase, 10 μl of 1 mg/ml NBT, and 100 μl of malstat reagent in each well of the 96-well plate. The absorbance was measured at 650 nm using a plate reader and was always proportional to the parasitemia detected by Giemsa-stained blood smears.

Uptake Assays of Nucleosides and Nucleobases on Free Trophozoites

Wild-type and pfnt1Δ-infected RBCs were synchronized using sorbitol (Lambros, C. & Vanderberg, J. P. (1979) *J Parasitol*, 65, 418-20) and trophozoites harvested by centrifugation at 720×g for 5 min at 4° C. The cell pellet was gently resuspended in cold PBS containing 0.005% saponin and again centrifuged as described above. The pellet was washed three times in cold PBS, resuspended in cold PBS supplemented with 20 mM glucose, and used immediately for transport assays. The cells were incubated with either 1 μM [$^3$H] adenosine (40.3 Ci/mmol), [$^3$H]inosine (50 Ci/mmol), [$^3$H] hypoxanthine (30 Ci/mmol), [$^3$H]guanine (11.8 Ci/mmol), or [$^3$H]isoleucine (92 Ci/mmol) at 37° C. or 4° C. for 1.5 min (linear phase of uptake), after which they were rapidly applied to glass fiber filters and washed twice with 5 ml of cold PBS. Filters were dried and counted by scintillation spectrometry.

Example 1

Disruption of the PfNT1 Gene in pKEΔPfNT Parasites

To evaluate the importance of PfNT1 in parasite development and survival, the generation of transgenic parasites lacking PfNT1 was attempted by a targeted gene replacement approach (Duraisingh, M. T., Triglia, T. & Cowman, A. F. (2002) *Int J Parasitol*, 32, 81-9). To achieve this goal, a targeting vector pKEΔPfNT was constructed (FIG. 1A). The overall knockout strategy entails a two step process by which PfNT1 is first interrupted with the blasticidin-s-deaminase (BSD) (Mamoun, C. B., Gluzman, I. Y., Goyard, S., Beverley, S. M. & Goldberg, D. E. (1999) *Proc Natl Acad Sci USA*, 96, 8716-20) cassette after a double cross-over event (FIG. 1A) followed by loss of the episome after selection against thymidine kinase (TK) gene expression. This targeted gene disruption strategy with double cross-over caused a 255 bp truncation in the middle of the PfNT1 open reading frame (ORF). Since loss of PfNT1 was conjectured to be a potentially lethal event (if PfNT1 is the major route of purine salvage in *P. falciparum*), pfnt1Δ mutants were selected in medium supplemented with 1.5 mM hypoxanthine, a concentration ~300-fold above that required for optimal growth of wild-type parasites. Transgenic parasites harboring the pKEΔ-PfNT targeting vector were first selected on blasticidin, then were treated with ganciclovir to eliminate parasites containing the targeting cassette in an episomal form. Parasites were cloned by limiting dilution and genomic DNA from cloned parasites purified for molecular analysis. Diagnostic PCR analysis using various combinations of primer pairs demonstrated the integration of the PfNT1.5'-BSD-PfNT1.3' cassette into the PfNT1 locus and the absence of intact wild type PfNT1 in 59 individual clones (not shown). Southern blot analyses on genomic DNA using various restriction digestions and probes specific for PfNT1 or BSD further confirmed disruption of the PfNT1 chromosomal locus by a double cross over event (FIG. 1B).

Example 2

Loss of Expression of PfNT1 in the pfnt1Δ Knockout

Figure 2:
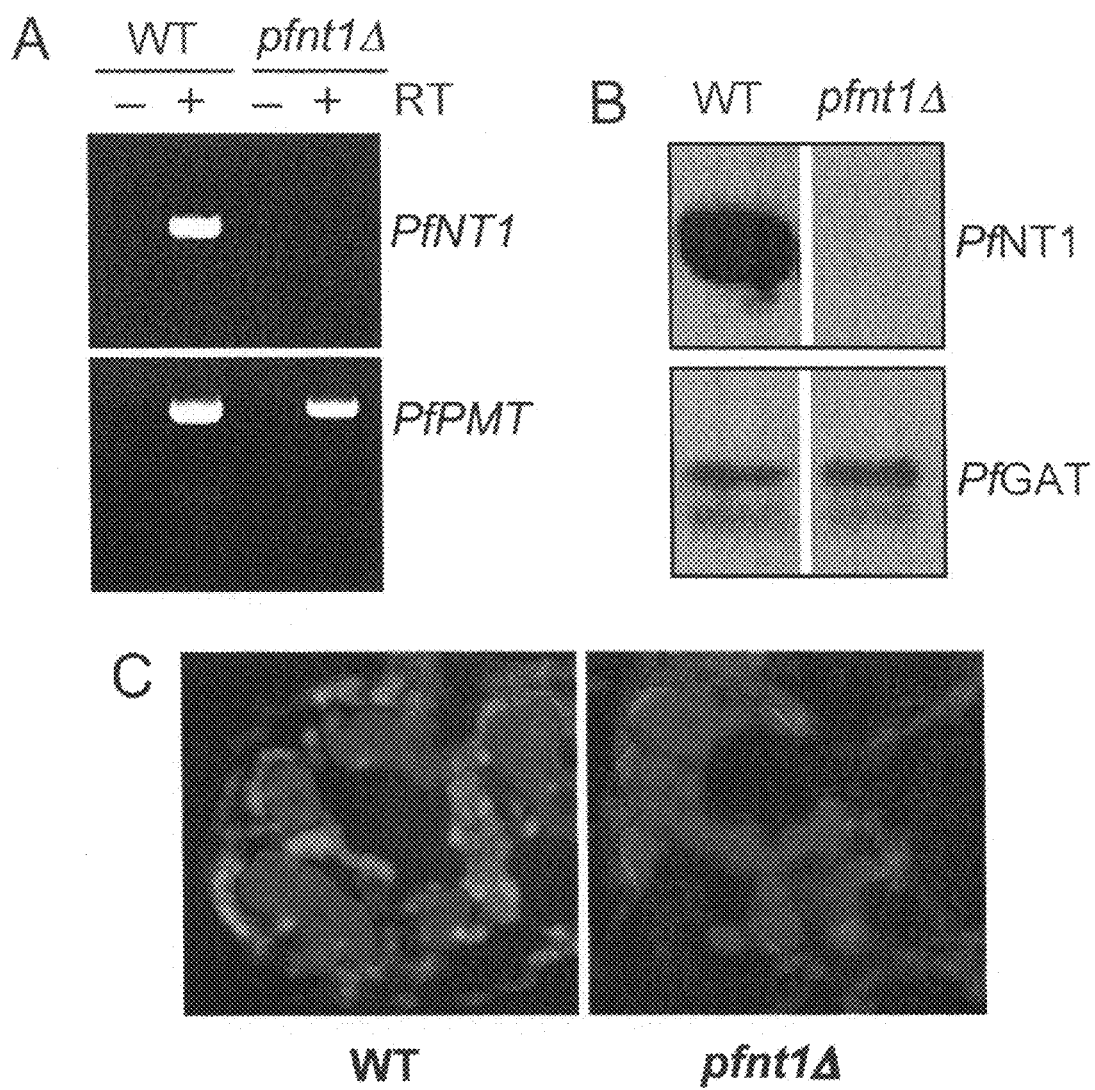
FIG. 2 illustrates the altered expression of PfNT1 in the pfnt1Δ strain; (A) RT-PCR analysis of RNA isolated from wild-type (WT) and pfnt1Δ strains using specific primers within the PfNT1 ORF. RT-PCR of the PfPMT cDNA is used as control. (B) Western blot analysis was performed using protein extracts from asynchronous cultures of wild-type and pfnt1Δ strains using PfNT1 antibodies; The glycerol-3-phosphate acyltransferase, PfGat, was used as an internal positive control. (C) Immunofluorescence microscopy of wild-type- and pfnt1Δ-infected RBCs at the schizont stage; DNA was counterstained with Hoechst dye (blue); In green, PfNT1 conjugated to the FITC-conjugated goat anti-rabbit secondary antibody; In red, Band 3 conjugated to Texas Red-conjugated anti-mouse secondary antibody.

To demonstrate the loss of PfNT1 expression in a pfnt1Δ clone, RT-PCR analysis was performed on RNA purified from wild-type and knockout parasites using primers within the PfNT1 ORF. PfNT1 cDNA was amplified from wild-type but not pfnt1Δ RNA (FIG. 2A). Loss of PfNT1 expression was further analyzed by immunoblotting using affinity-purified anti-PfNT1 antibodies (Rager, N., Mamoun, C. B., Carter, N. S., Goldberg, D. E. & Ullman, B. (2001) *J Biol Chem*, 276, 41095-9). Whereas a 46 kDa PfNT1 band was detected in wild-type *P. falciparum*, no signal was identified in the pfnt1Δ parasites (FIG. 2B). As a loading control, antibodies raised against the parasite endoplasmic reticulum membrane protein PfGat (Santiago, T. C., Zufferey, R., Mehra, R. S., Coleman, R. A. & Ben Mamoun, C. (2004) *J Biol Chem*, 279, 9222-32) were used, and the expected 64 kDa PfGat band was observed in both the wild-type and pfnt1Δlysates (FIG. 2B). Immunofluorescence analysis corroborated the loss of PfNT1 expression in the pfnt1Δ clone and verified its localization to the PPM in wild type *P. falciparum* (FIG. 2C) (Rager, N., Mamoun, C. B., Carter, N. S., Goldberg, D. E. & Ullman, B. (2001) *J Biol Chem*, 276, 41095-9).

Example 3

Purine Requirements for pfnt1Δ Parasites

Figure 3:
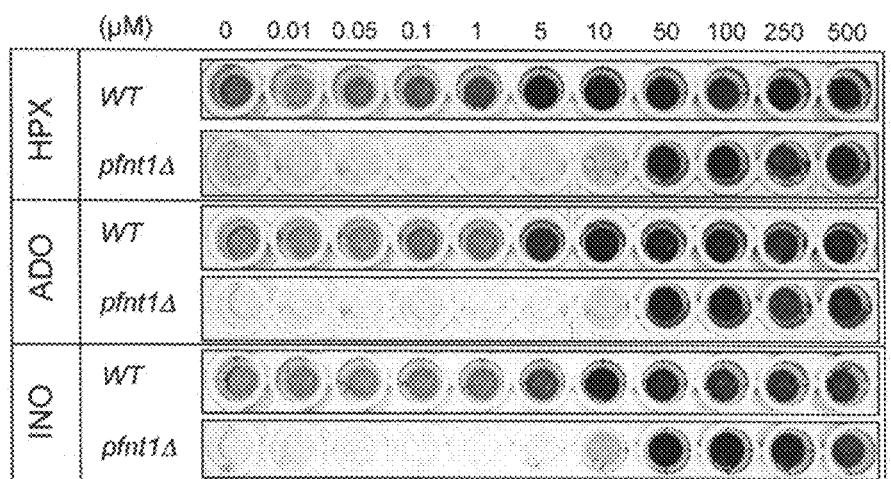
FIG. 3 illustrates the growth of pfnt1Δ parasites in the presence of increasing concentrations of hypoxanthine (HPX), adenosine (ADO) or inosine (INO); (A) Parasite-specific lactate dehydrogenase assay, pLDH, to detect the growth of the parasites; (B) Synchronized WT and pfnt1Δ parasites grown at different concentrations of hypoxanthine (0, 2, 5, 100, and 1500 µM), were collected at different stages and analyzed by Giemsa stain, and evaluated by light microscopy.
Figure 3:
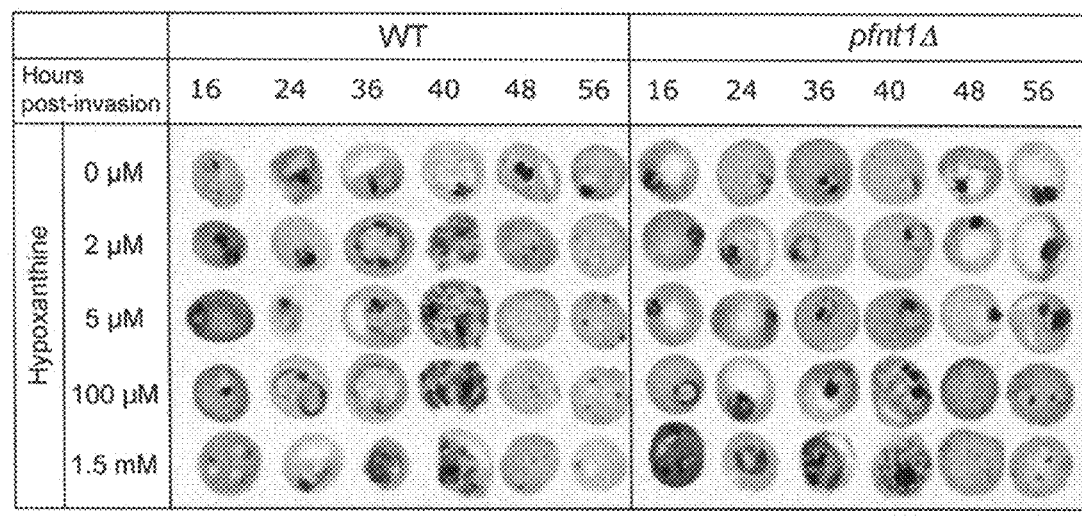

To assess the role of PfNT1 in purine acquisition during the parasite intraerythrocytic life cycle, wild-type and pfnt1Δ *P. falciparum* were grown in the presence of increasing concentrations of hypoxanthine, adenosine or inosine, and parasite growth was monitored by measuring parasite LDH production. Whereas optimal growth was observed in the wild-type parasites at purine concentrations of 5 μM and above, pfnt1Δ parasites were not viable in adenosine, inosine, or hypoxanthine at concentrations below 50 μM (FIG. 3A). To measure the impact of the pfnt1Δ lesion on parasite intraerythrocytic development, wild-type and pfnt1Δ cells were synchronized and cultured in the absence or presence of increasing concentrations of hypoxanthine. Parasite progression through the life cycle (ring>trophozoite>schizont>ring) was monitored at various times after erythrocyte invasion. For both strains lack of purine resulted in blockage of growth at the ring stage (FIG. 3B). However, whereas wild-type *P. falciparum* completed their entire intraerythrocytic cycle at concentrations of hypoxanthine as low as 2 μM (FIG. 3B), pfnt1Δ mutants required significantly higher concentrations of hypoxanthine to progress from the ring stage of development (FIG. 3B). Similar results were obtained with adenosine and inosine (not shown). Concentrations of hypoxanthine between 100 μM and 1.5 mM restored parasite progression throughout the cell cycle, although the growth of pfnt1Δ was slower than that of the wild-type strain at concentrations below 500 μM (not shown). These results demonstrate that under physiological purine concentrations (between 0.4 and 6 μM (Traut, T. W. (1994) *Mol Cell Biochem*, 140, 1-22) PfNT1 is essential for the intraerythrocytic development of the parasite and that at higher concentrations hypoxanthine, adenosine and inosine could be transported via a secondary mechanism. Parasite utilization of adenosine and inosine could be either via direct transport of these substrates or via conversion of the nucleosides into hypoxanthine by the sequential actions of ADA and PNP, respectively, prior to hypoxanthine uptake via PfNT1 (see below).

Example 4

Transport of Purines by pfnt1Δ Parasites

Figure 4:
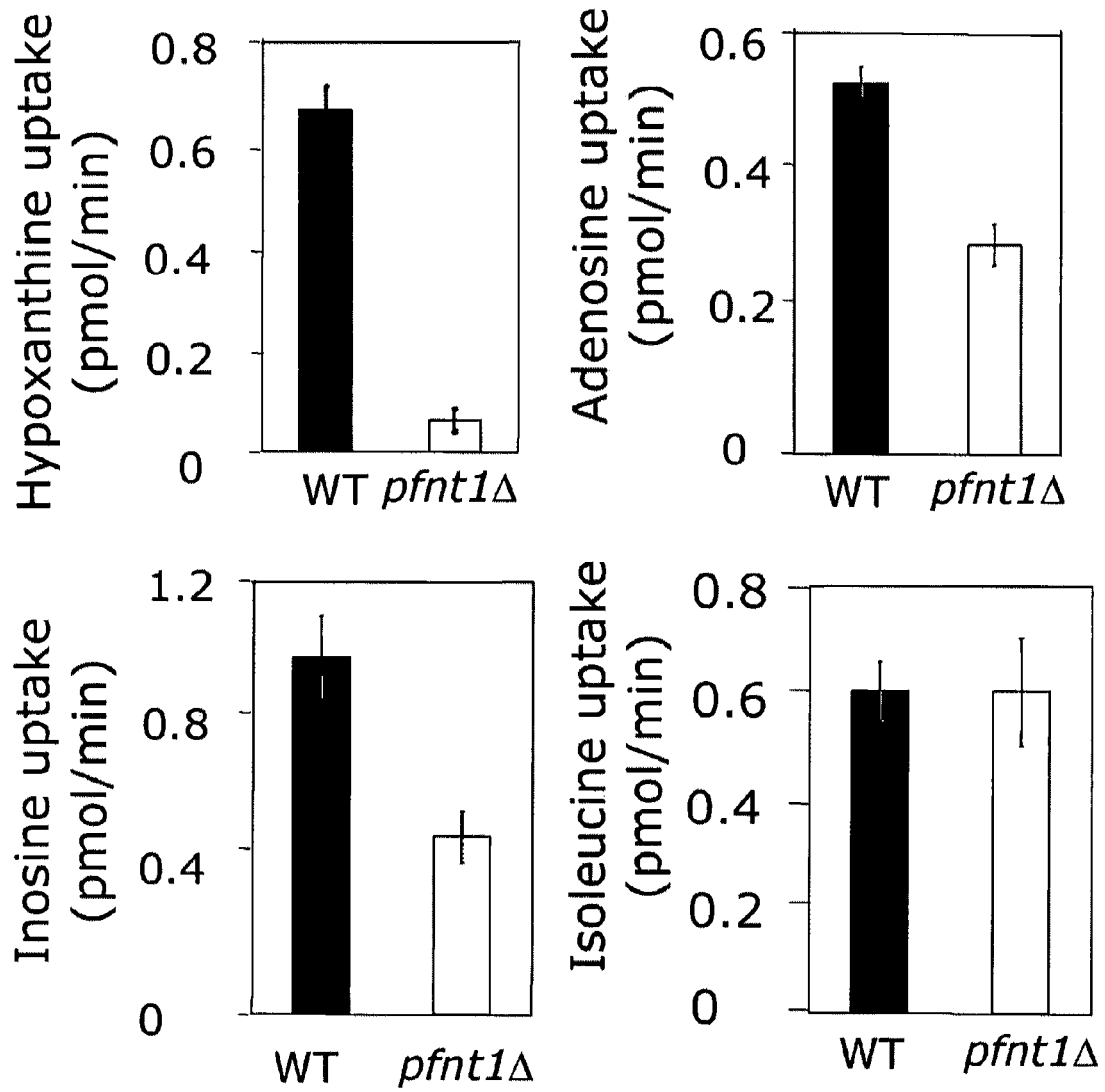
FIG. 4 illustrates purine uptake in wild-type (WT) and pfnt1Δ free parasites; Uptake of hypoxanthine, adenosine and inosine in free wild-type (WT) and pfnt1Δ trophozoites was performed as described in Materials and Methods; isoleucine uptake is used as a control; These experiments were performed at least three times and each value is the mean±standard deviation of at least triplicate experiments.

The inability of pfnt1Δ to grow at physiological concentrations of purine suggests that PfNT1 is the major route of purine translocation across the PPM. To test this supposition, both wild-type and pfnt1Δ parasites were purified from erythrocytes and their ability to transport radiolabeled hypoxanthine, adenosine, and inosine measured. Whereas the transport of adenosine and inosine was only diminished slightly in the pfnt1Δ strain, the transport of hypoxanthine was dramatically reduced when compared to its wild-type parent (FIG. 4). These differences in transport between wild-type and pfnt1Δ parasites did not arise from general discrepancies in translocation across the PPM since transport of isoleucine was identical in both strains (FIG. 4). The ability of erythrocyte-liberated pfnt1Δ parasites to effectively transport adenosine and inosine demonstrates that the PPM harbors one or more additional permeases capable of transporting these nucleosides.

Example 5

Figure 5:
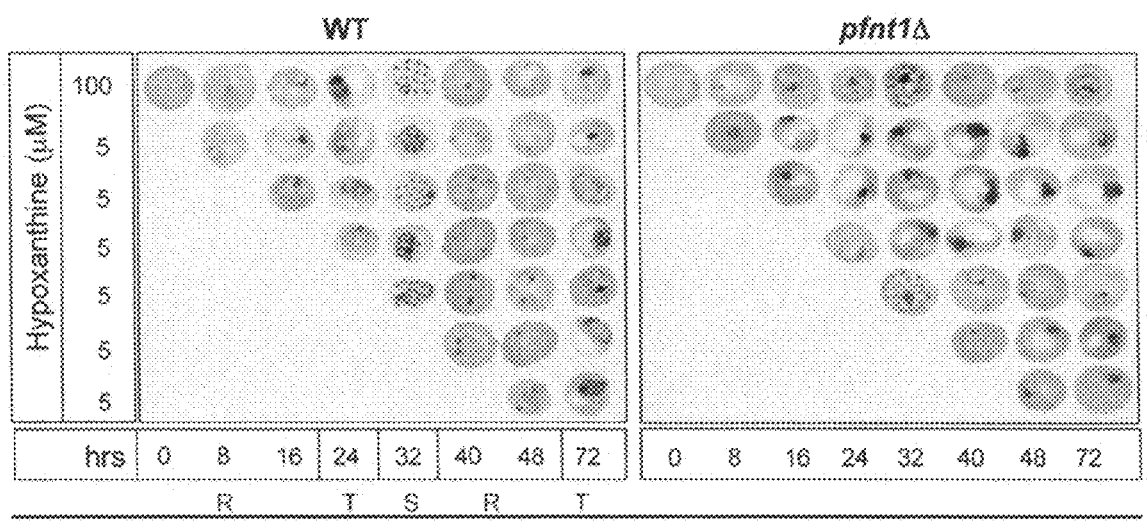
FIG. 5 illustrates that PfNT1 is required for parasite intraerythrocytic development but not essential for rupture of schizont-infected erythrocytes or invasion; Wild-type (WT) and pfnt1Δ strains were synchronized and at different stages (rings (R), trophozoite (T) and schizont (S)) transferred from medium containing 100 μM of hypoxanthine to medium containing 5 μM of this substrate; Parasite development was then monitored every 8 hours post starvation by Giemsa staining and microscopy.

PfNT1 is Essential for Intraerythrocytic Development but not for Erythrocyte Invasion To determine whether the pfnt1 lesion is deleterious to *P. falciparum* parasites at all stages of intraerythrocytic development, wild-type and pfnt1Δ strains were synchronized and transferred at either ring, trophozoite or schizont stage from medium containing 100 μM of hypoxanthine to medium containing 5 μM hypoxanthine and their continued development monitored. While wild-type parasites exhibited normal progression from stage to stage throughout their entire intraerythrocytic development, pfnt1Δ parasites failed to transform from ring to trophozoite or from trophozoite to schizont stage (FIG. 5). The reduction in exogenous hypoxanthine concentration did not affect, however, the ability of pfnt1Δ merozoites to invade new erythrocytes following the rupture of infected erythrocytes during schizogony (FIG. 5).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A composition for eliciting an immune response in a host, comprising a live *Plasmodium falciparum* malarial parasite with a conditionally lethal mutation and a pharmaceutically acceptable carrier, wherein the mutation is that a nucleoside transporter 1 (NT1) gene has been rendered nonfunctional.

2. The composition of claim 1, wherein the *P. falciparum* is selected from the group consisting of a falciparum 3D7 strain, a falciparum Vietnam-Fort (FVO) strain, a falciparum Uganda-Palo Alto (FUP) strain, a falciparum FCH/4 (Philippines) strain, a falciparum Santa Lucia (Salvador I) strain, and a falciparum Malayan Camp (MC) strain.

3. The composition of claim 1, wherein the NT1 gene is rendered non-functional by knockout technology or homologous recombination.

4. The composition of claim 1, wherein the malarial parasite further comprises an additional non-functional gene when present in naturally occurring form, encodes a protein necessary for the intraerythrocytic development of the malarial parasite.

5. The composition of claim 1 combined with an adjuvant.

6. A method of eliciting an immune response in a host, comprising introducing into the host an effective amount of the composition of claim 1, wherein the composition is introduced in an amount sufficient to elicit an immune response.

7. The method of claim 6, wherein the host is a human.

8. The method of claim 6, wherein the composition is administered to the host by injection.

9. The method of claim 6, wherein the composition is administered to the host by injection of the composition on multiple days.

10. The method of claim 6, wherein the composition is administered with an adjuvant.

11. A composition for immunization, comprising more than one of the *P. falciparum* strains of claim 2.

12. A method of producing the composition of claim 1, comprising the following steps:

preparing a live *Plasmodium falciparum* malarial parasite with a conditionally lethal mutation by using knockout technology or homologous recombination to render non-functional a Nucleoside Transporter 1 (NT1) gene;

growing and propagating the malarial parasite using a growth medium comprising a higher than physiological concentration of one or more essential nutrients;

isolating the parasite from the growth medium; and adding a pharmaceutically acceptable carrier to the isolated parasite.

13. The method of claim 12, further comprising:

exposing the isolated malarial parasite for a length of time to a medium comprising physiological concentrations of essential nutrients.

* * * * *